(12) United States Patent
Nikolic et al.

(10) Patent No.: US 11,759,555 B2
(45) Date of Patent: Sep. 19, 2023

(54) PRINTABLE ELECTRICAL COMPONENT COMPRISING A PLASTIC SUBSTRATE

(71) Applicant: FRESENIUS MEDICAL CARE DEUTSCHLAND GMBH, Bad Homburg (DE)

(72) Inventors: Dejan Nikolic, Bad Soden (DE); Alexander Heide, Eppstein (DE); Daniel Juric, Stuttgart (DE); Andre Buelau, Stuttgart (DE); Juergen Keck, Filderstadt (DE); Jonathan Seybold, Blaufelden (DE); Karl-Peter Fritz, Schonaich (DE); Kerstin Glaeser, Boeblingen (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 0 days.

(21) Appl. No.: 17/766,536

(22) PCT Filed: Oct. 9, 2020

(86) PCT No.: PCT/EP2020/078352
§ 371 (c)(1),
(2) Date: Apr. 5, 2022

(87) PCT Pub. No.: WO2021/069631
PCT Pub. Date: Apr. 15, 2021

(65) Prior Publication Data
US 2022/0369471 A1    Nov. 17, 2022

(30) Foreign Application Priority Data
Oct. 11, 2019    (DE) ............... 10 2019 215 595.2

(51) Int. Cl.
*A61M 1/14* (2006.01)
*A61M 1/36* (2006.01)
(Continued)

(52) U.S. Cl.
CPC ............. *A61M 1/14* (2013.01); *A61M 1/34* (2013.01); *A61M 1/36* (2013.01); *A61M 1/3639* (2013.01);
(Continued)

(58) Field of Classification Search
CPC .......... A61M 1/14; A61M 1/154; A61M 1/34; A61M 1/36; A61M 1/36224;
(Continued)

(56) References Cited

U.S. PATENT DOCUMENTS

2010/0119789 A1 * 5/2010 Grande ............... C09D 11/52
977/734
2013/0133934 A1 5/2013 Flores et al.
(Continued)

FOREIGN PATENT DOCUMENTS

CA      2999499 A1 * 9/2014
DE  102015005781 A1   11/2016
(Continued)

OTHER PUBLICATIONS

International Search Report and Written Opinion issued in corresponding International Patent Application No. PCT/EP2020/078352 (with English translation of International Search Report) dated Apr. 6, 2021 (21 pages).
(Continued)

*Primary Examiner* — John Kim
(74) *Attorney, Agent, or Firm* — Kilyk & Bowersox, P.L.L.C.

(57) ABSTRACT

The invention relates to a medical device comprising a printable electrical component (1), the printable electrical
(Continued)

component (1) comprising a plastic substrate (L1) wherein at least electrical component (E) is applied to the plastic substrate, wherein the electrical component (E) comprises a dried conductive ink, wherein the plastic substrate is selected from the group comprising polycarbonate, cycloolefin copolymers, polymethylacrylate, polypropylene and wherein the dried conductive ink comprise silver and/or gold, wherein the electrical component (E) comprises feather-like and/or meander-like and/or spiral-shaped sections, whereby the medical device further comprises a fluid line, wherein the printable electrical component is located on the outside of the fluid line. The invention also relates to a medical device comprising a printable electrical component (1) the printable electrical component (1) comprising a plastic substrate (L1), wherein at least one electrical component (E) is applied to the plastic substrate, wherein the electrical component (E) comprises a dried conductive ink, wherein the plastic substrate is selected from a group comprising polycarbonate, cycloolefin copolymers, polymethyl-methacrylate, polypropylene and wherein the dried, conductive ink comprises silver and/or gold, wherein the electrical component (E) comprises at least one conductor section or at least two electrodes, characterized in that the electrical component (E) is part of an expansion sensor and/or a pressure sensor and/or a thermal flow sensor.

11 Claims, 4 Drawing Sheets

(51) Int. Cl.
  *H05K 3/12* (2006.01)
  *H05K 1/16* (2006.01)
  *H05K 3/10* (2006.01)
  *H05K 1/09* (2006.01)
  *A61M 1/34* (2006.01)

(52) U.S. Cl.
  CPC .......... *A61M 1/36224* (2022.05); *H05K 1/09* (2013.01); *H05K 1/092* (2013.01); *H05K 1/16* (2013.01); *H05K 3/10* (2013.01); *H05K 3/125* (2013.01); *A61M 1/154* (2022.05); *H05K 2201/09263* (2013.01); *H05K 2201/10151* (2013.01); *H05K 2203/1131* (2013.01)

(58) Field of Classification Search
  CPC ....... A61M 1/3639; H05K 1/09; H05K 1/092; H05K 1/16; H05K 3/10; H05K 3/1241; H05K 3/125; H05K 1/162; H05K 1/165; H05K 1/167; H05K 2201/09263; H05K 2201/10151; H05K 2203/1131
  See application file for complete search history.

(56) References Cited

U.S. PATENT DOCUMENTS

| | | |
|---|---|---|
| 2015/0037550 A1 | 2/2015 | Balasubramaniam et al. |
| 2018/0088072 A1 | 3/2018 | Yakushenko et al. |
| 2018/0149531 A1 | 5/2018 | Atashbar et al. |
| 2020/0016316 A1 | 1/2020 | Heide et al. |
| 2020/0093974 A1* | 3/2020 | Heide .................... A61M 1/14 |

FOREIGN PATENT DOCUMENTS

| | | | |
|---|---|---|---|
| DE | 102017106403 A1 | | 9/2018 |
| EP | 2305108 A1 | | 4/2011 |
| EP | 3476287 A2 | | 5/2019 |
| WO | 2012171936 A1 | | 12/2012 |
| WO | 2018172364 A1 | | 9/2018 |
| WO | WO 2018/172364 | * | 9/2018 |

OTHER PUBLICATIONS

Office Action issued in corresponding German Patent Application 10 2019 215 595 2 dated May 27, 2020 (with English translation)(18 pages).
Office Action issued in corresponding German Patent Application 10 2019 215 595.2 dated Apr. 30, 2021 (with English translation)(8 pages).
Bessonov et al., "Flexible and Printable Sensors," Nanotechnologies in Russia, 2015, vol. 10, Nos. 3-4, pp. 165-180.

* cited by examiner

PRINTABLE ELECTRICAL COMPONENT COMPRISING A PLASTIC SUBSTRATE

This application is a National Stage Application of PCT/EP2020/078352, filed Oct. 9, 2020, which claims priority to German Patent Application No. 10 2019 215 595.2, filed Oct. 11, 2019.

The invention relates to a printable electrical component comprising a plastic substrate.

BACKGROUND

In almost all areas of life electronic devices are used today. As a rule, electronic components are also used for the most varied of purposes.

Electronic components are used in particular for measuring purposes.

In the field of medicine too—whether it be for diagnosis or therapy—electronic components are used, especially for measuring purposes.

For example a printable sensor for wearing on the skin is known from the european patent document EP 2 305 108 B1.

Using the example of a dialysis device, for example, such measuring purposes can be explained.

During dialysis—without being restricted here to a particular form of dialysis—it may be desirable or necessary to measure and record certain parameters. For example, values relating to the current condition of the patient, as well as functional dialysis values can be recorded. For instance, pulse, blood pressure values (systolic, diastolic), oxygen saturation etc. can be recorded as examples of non-invasively measurable values. Equally, weights, quantities, pressures, pH values, creatinine values etc. of fluids can be measured in connection with the dialysis.

Particularly for dialysis-specific values, sensors have been provided on the respective devices. However, in doing so it must be ensured that the hygienic requirements are met. On the one hand this can be achieved by disinfecting the relevant sensors after each patient, or in that through an appropriate design of the sensors such disinfection is not necessary.

However, the disinfection of parts of a dialysis device after every patient is very time-consuming. In the past, this time expenditure has repeatedly resulted in the hygiene requirements being reduced at the expense of the patients. Therefore, as an alternative, sensors were developed which no longer come into direct contact with elements which would otherwise have to be disinfected. For example, this can be achieved in that pressure sensors are applied from outside onto flexible elements through which fluids flow. Also, through an appropriate pump design the quantity flowing through, for example, can be determined by way of the pump action.

However, this approach also has disadvantages. One drawback is that the now required sensor must record the measurements with considerably greater precision as the measurement is now indirect and no longer direct. On the other hand the design must be tailored to the special requirements of the sensors in order to prevent incorrect measurements—e.g. through incorrectly inserted fluid connections. However, these design measures are also expensive.

Against this background, the aim of the invention is to propose solutions that allow electronic components to be provided especially for measuring purposes and in particular for medical purposes.

This aim is achieved through a medical device comprising a printable electrical component, the printable electrical component comprising a plastic substrate, wherein applied on the plastic substrate is at least one electrical component, wherein the electrical component comprises a dried conductive ink, wherein the plastic substrate is selected from a group comprising polycarbonate, cycloolefin copolymers, polymethylmethacrylate, poly-propylene and wherein the dried conductive ink comprises silver and/or gold, and wherein the electrical component has feather-like and/or meander-like and/or spiral-shaped sections, whereby the printable electrical component is located on the outside of the fluid line.

The aim is also achieved through a medical device comprising a printable electrical component, the printable electrical component comprising a plastic substrate, wherein applied on the plastic substrate is at least one electrical component, wherein the electrical component comprises a dried conductive ink, wherein the plastic substrate is selected from a group comprising polycarbonate, cycloolefin copolymers, polymethylmethacrylate, poly-propylene and wherein the dried conductive ink comprises silver and/or gold, and wherein the electrical component comprises at least one conductor section or at least two electrodes, characterized in that the electrical component is part of a an expansion sensor and/or a thermal flow sensor.

In particular, the aim is achieved by way of a wearable for wearing on the body and comprising such a medical device.

The aim is also achieved by a method of producing such a printable electrical component, comprising the stage of obtaining a plastic substrate, applying a conductive ink onto the plastic substrate, wherein the conducive ink comprises silver and/or gold, and drying the conductive ink.

Other advantageous embodiments form the subject matter of the respective dependent claims, the figure and the description.

BRIEF DESCRIPTION OF THE DRAWINGS

The invention will be explained below in more detail with reference to the figures. Here

The invention will be described below in more detail with reference to the figures. It should be noted that different aspects will be described, which can be used individually or in combination. This means that each aspect can be used with different forms of embodiment of the invention unless explicitly described as a pure alternative.

Also, for the sake of simplicity, in the following only one entity is always referred to as a rule. However, unless explicitly stated the invention the invention can also have several of the entities in question. To this extent, the use of the words "a" and "an" should be understood an indication that in a simple form of embodiment at least one entity is used.

If processes are described below, the individual stages of a process can be arranged and/or combined in any sequence unless indicated otherwise by the context. In addition—unless expressly stated otherwise—the processes can be combined with each other.

As a rule numerical values are not to be understood as exact values, but contain a tolerance of +/−1% to +/−10%.

In forms of embodiment of the invention a printable electrical component 1 is provided. The printable electrical component 1 comprises a plastic substrate L1. Preferably the plastic substrate L1 is flexible. In relation to its area the plastic substrate is thus thin, e.g. 2 mm or thinner.

At least one electrical component E is applied to the plastic substrate L1. For this the plastic substrate L1 can be previously prepared by means of a plasma process.

The electrical component E comprises a dried, conductive ink. This conductive ink can be previously applied by way of a suitable process, e.g. an aerosol jet printing process or an inkjet printing process, where this is only listed as an example. Examples of inks are, for instance, nanoparticle inks.

The plastic substrate L1 is a polymer material, wherein the process of production is unimportant for the following description of the invention. More particularly the plastic substrate L1 is selected from a group comprising polycarbonate, cycloolefin copolymers, polymethylacrylate, polypropylene. The plastic substrate L1 can comprise Makrolon® OD2015 as an example of a polycarbonate.

The dried conductive ink comprises a metal or an alloy. In particular, the conductive ink comprises silver and/or gold and/or nickel and/or copper. Preferably the conductive ink comprises silver.

An electrical component E can also be understood to be a printed electrical circuit structure.

Figure 2:
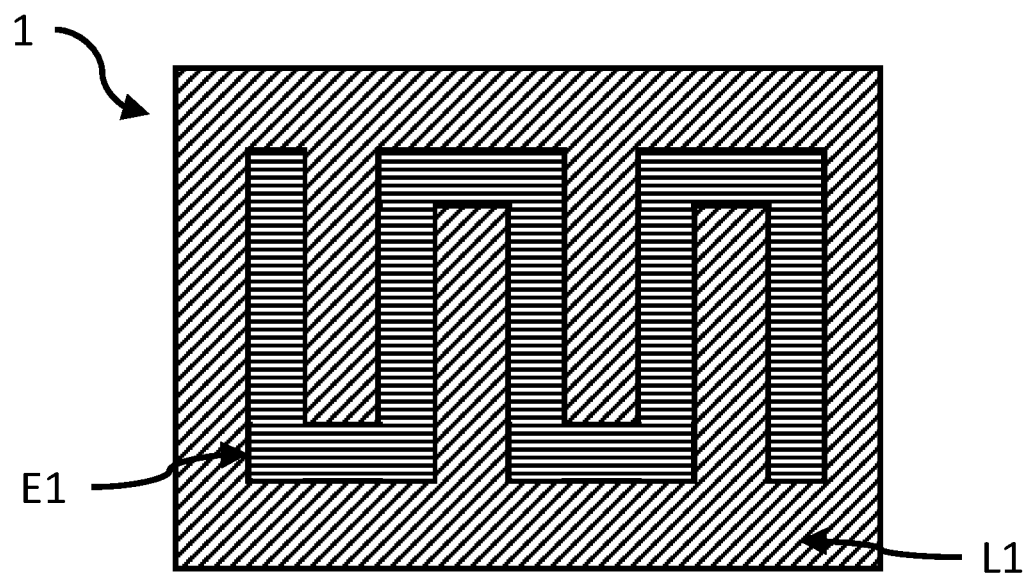
FIGS. 2-4, 6 each show a schematic view of a printable electrical component according to the invention in accordance with forms of embodiment of the invention.
Figure 3:
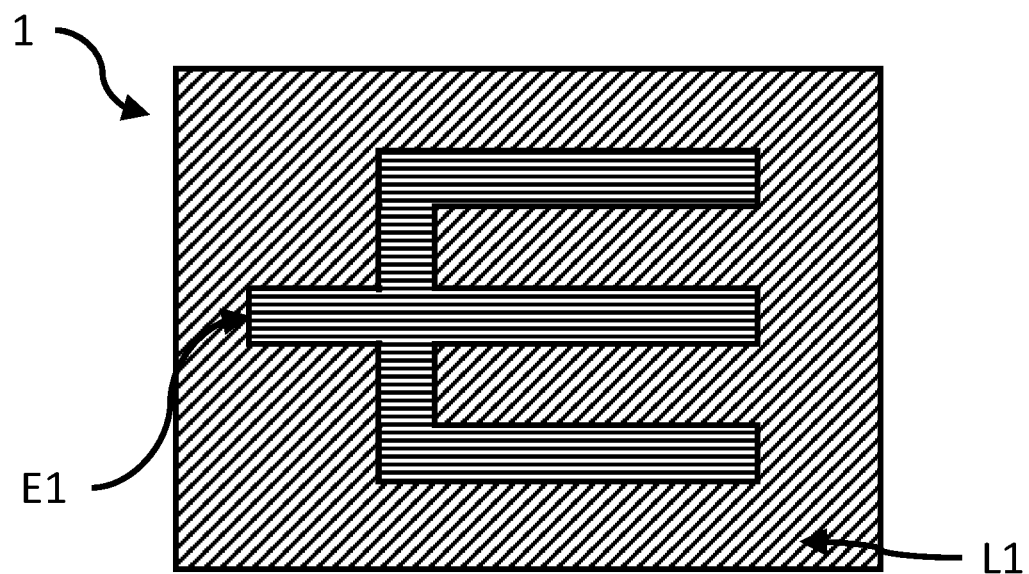
Figure 4:
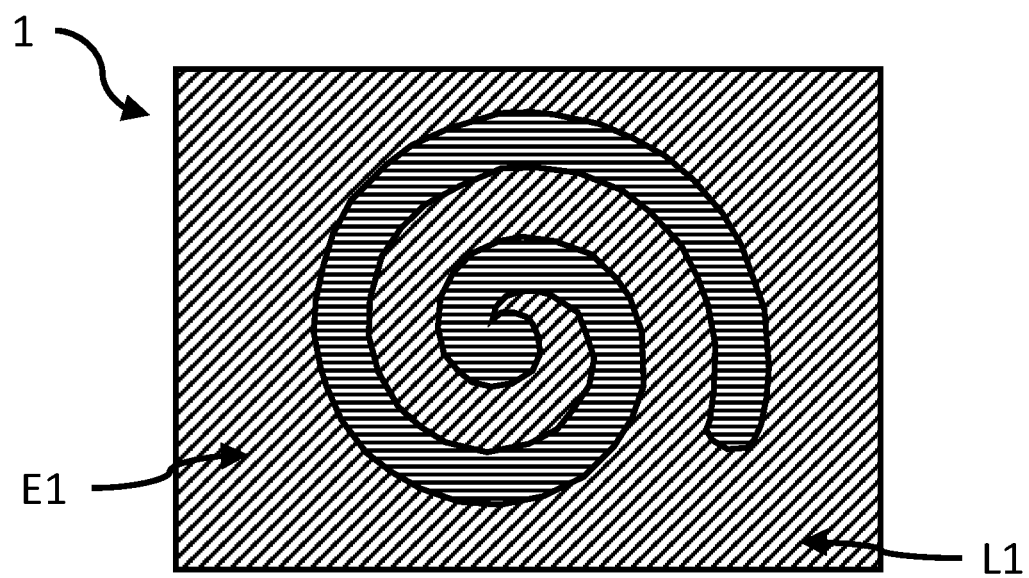
Figure 6:
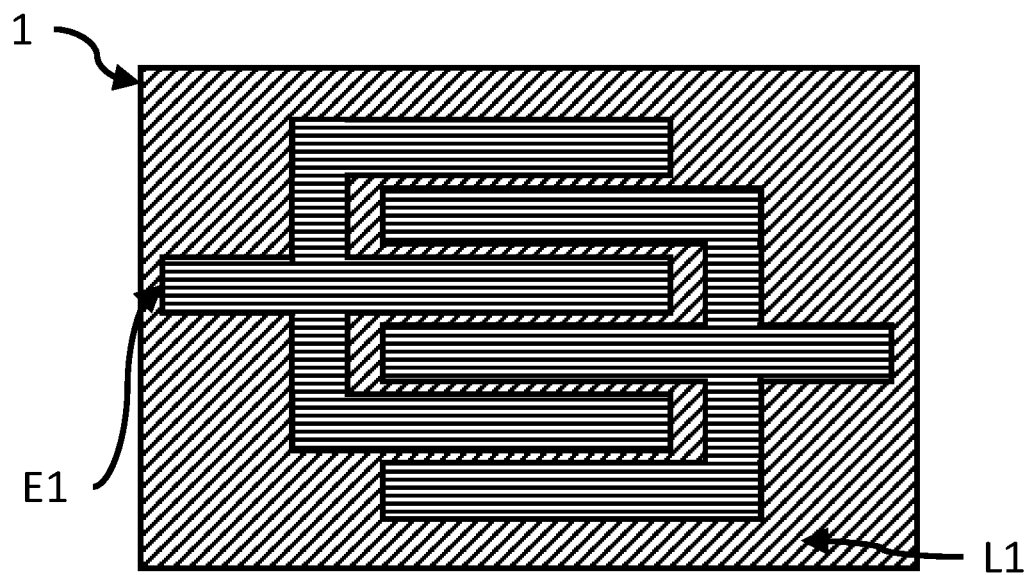

By way of the dried conductive ink (which can also be applied multiple times and be the subject matter of pre- and/or post-processing stages) at least one conductor section or at least two electrodes is/are formed. The conductor section can form the electrical component E. The electrical component E can, for example, as shown in FIG. 2, have meander-like and/or—as shown in FIG. 3—have feather-like and/or—as shown in FIG. 4—have spiral-shaped sections or an elongated section, wherein different shapes can be combined with each other. An electrical component E differs from a purely electrical connection in that under the influence of environmental conditions it can be measurable changed in terms of its electrical properties. In other words, there is a change in resistance and/or capacitance and/or inductivity. For example, two feather-like structures together can form a capacitor—as shown in FIG. 6. Meander-like structures—as shown in FIG. 2—and/or spiral-shaped sections—as shown in FIG. 4, can, for example, assume the function of an expansion measuring strip. In addition, all forms can also act as a temperature-dependent resistor. Also, for example, two electrodes can be provided with which, for example, a resistance/conductance value of a fluid in contact with the electrodes can be measured.

More particularly, the printable electrical component 1 can be provided on a plastic substrate L1 comprising cycloolefin copolymers and a dried ink containing silver. Equally, the printable electrical component 1 can be provided on a plastic substrate L1 comprising cycloolefin copolymers and a dried ink containing gold. The printable electrical component 1 can also be provided on a plastic substrate L1 comprising polycarbonate and a dried ink containing silver. Furthermore the printable electrical component 1 can be provided on a plastic substrate L1 containing polycarbonate and a dried ink containing gold.

Figure 7:
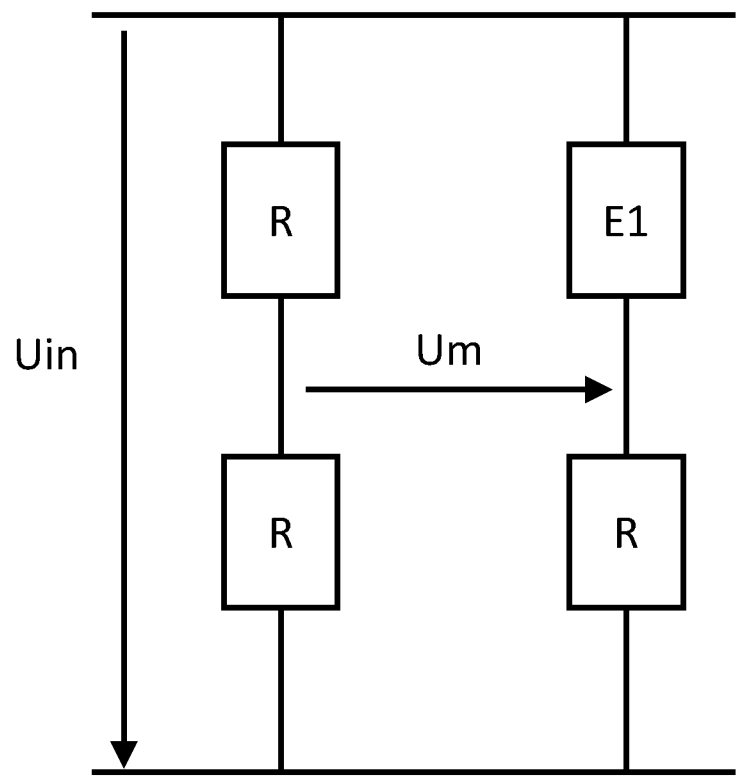
FIG. 7 shows an electrical equivalent circuit diagram for using printable electrical components according to the invention in accordance with forms of embodiment of the invention.

In one form of embodiment of the invention the electrical component E is part of a sensor. For example, with such an electrical component a resistance measuring bridge can be built up in which the change compared with a known identical component under the effect of environmental influences is evaluated. An example is a Wheatstone bridge as shown in FIG. 7. In this way, with an applied voltage Uin the change due to environmental influences in relation to the electrical component E can be measured as a change in voltage. For this, suitable analogue or digital processing of the measuring signal can follow, e.g. by means of an operational amplifier and/or an analogue-digital converter.

For example, in this way an expansion sensor and/or a temperature sensor and/or a conductivity sensor and/or a pressure sensor and/or a thermal flow sensor can be provided.

In a particularly advantageous embodiment the printable electrical component 1 is biocompatible. In other words the printable electrical component can be arranged both on the body and also in the body, as well as come into contact with fluids supplied to the body without the risk of harm to the body arising.

In another advantageous embodiment the printable electrical component 1 is not biodegradable, i.e. substances supplied to a body can be in contact for a long time. In this way, for example, monitoring devices which monitor the stability of a fluid supplied to the body, or sensor devices which are only required when a fluid is used, can be integrated into a container or fluid line without the danger of damage occurring or the risk that harmful substances are transferred into the fluid. In addition, such an arrangement also allows electrical components 1 to be left in a sterile area, through which patient safety can be improved.

Figure 1:
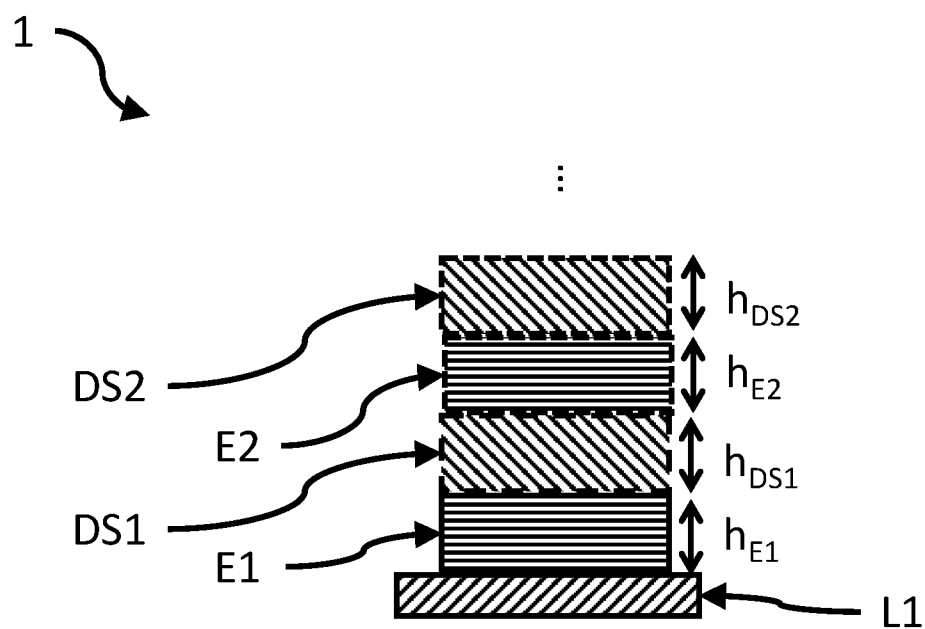
FIG. 1 shows a schematic cross-sectional view of aspects of a printable electrical component according to the invention in accordance with forms of embodiment of the invention.

In a further form of embodiment of the invention the dried conductive ink is covered with a protective layer. Such a protective layer can on the one hand be provided to protect against undesirable effects on the electrical element 1, e.g. to provide protection against certain gaseous components, moisture, contact. Additionally or alternatively, protection against the emergence of undesirable substances but also against undesirable chemical reactions can be also be provided in this way. In multiple-layer devices the protective layer can also be provided as an insulator between different levels. For example, in FIG. 1 a layering system is shown in which on the plastic substrate L1 in a first level of a certain height hE1 a first electrical component E1 is provided. Onto the first electrical component E1 a protective layer DS1 is applied on which in turn in a second level of a certain height hE2 a second electrical element E2 (produced in an analogue manner to E1) is provided. This "stack structuring" can be continued, whereby the selection of material for the individual layers is flexible. For example, it can be envisaged that the material systems are identical, i.e. the material for E1 and E2 is the same and/or the material for DS1 and DS2 is identical, or different. The heights hE1 and hE2 can also be the same or vary.

In one form of embodiment of the invention the protective layer acts in an electrically insulating manner, wherein onto the protective layer at least one further electrical component is applied, wherein the further electrical component comprises a dried conductive ink, wherein the plastic substrate is selected from a group comprising polycarbonate, cycoolefin copolymers, poly-methylacrylate, polypropylene and wherein the dried conductive ink comprises silver and/or gold.

In one form of embodiment of the invention the plastic substrate L1 comprises a textile material. The textile material can, for example, be woven or non-woven.

As already described previously, the invention can also be designed as a medical device that comprises a printable electrical component 1 of the previously described type.

According to one form of embodiment of the invention the medical device has a fluid line, wherein the printed electrical component E1 is located on the inner side of the fluid line, i.e. the printable electrical component E1 can directly measure properties of the fluid. These could be, for example, the pressure or the temperature or a concentration of a substance.

In accordance with an alternative form of embodiment of the invention the medical device comprises a fluid line, wherein the electrical component is located on the outer side of the fluid line, i.e. the printable electrical component E1 can indirectly measure properties of the fluid through the fluid line wall. These could be the pressure or the temperature for instance. On the other hand it would also be possible to measure environmental influences on the fluid line.

In forms of embodiment of the invention the medical device is an element of a dialysis machine. For example the medical product can be part of the analysis device or also of a consumable. Examples of consumables are dialysers, dialyser fluid filters, flexile tubes, flexible tube sets, cassettes with at least two fluid channels—in particular a blood cassette and/or dialysate cassette (this can, for example, have a hard plastic body), flow sensor, canister, needle connection area (comprising, for example, a blood cannula and a flexible tube for connection thereto), concentrate bag (containing bicarbonate for example), filtrate bag, heparin bag, substitute bag, dialysate bag. More particularly the medical product can also be disposable consumable of a dialysis device.

In a further embodiment of the invention a wearable is provided for wearing on the body which has a printable, electrical component 1 of the previously described type. The wearable itself can be worn on the body or the wearable is located on a corresponding fabric.

For example, the printable electrical component E1 can be arranged on an elastic strap so that the strap can be slung around the body or part of the body of a mammal in contact therewith. The strap itself can also act as a plastic substrate L1. In particular, the wearable can be a medical device for measuring vital parameters (respiratory activity, pulse, heart activity, electrical potentials) for example.

Without loss of generality, a printable electronic component according to the invention can be used in a dialysis system or in another therapeutic/diagnostic system.

The printable electrical component 1 of the proposed type can, for example, be produced in a process as described below as an example.

Hereby an (optionally pre-treated) plastic substrate is produced in a stage 100.

In stage 200, a conductive ink is applied to the plastic substrate L1. The conductive ink comprises sliver and/or gold. Preferably the conductive ink comprises silver.

The ink is then (actively or passively) dried, i.e. the solvent is evaporated and, amongst other things, the silver and/or the gold remains.

Optionally it can be envisaged that after finishing production a protective layer is applied to an electrical component in stage 500. For example, a protective layer DS1 can be applied after completing the production of E1.

Figure 5:
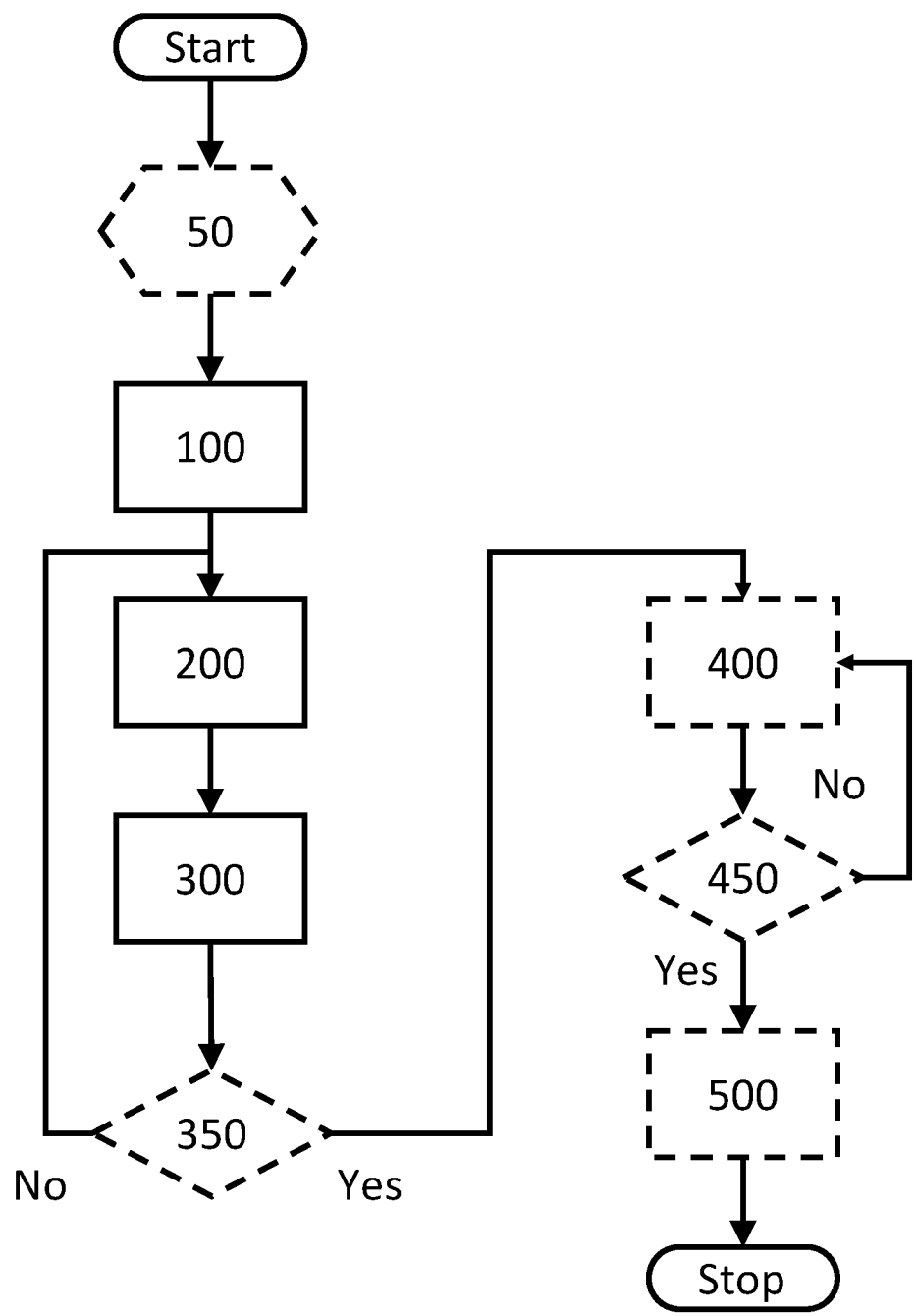
FIG. 5 shows a schematic flow diagram for producing printable electrical components in accordance with forms of embodiment of the invention.

In one form of embodiment of the invention, before the application of the conductive ink onto the plastic substrate L1, the plastic substrate is pre-treated with a plasma. This pre-treatment stage can, as indicated in FIG. 5, be envisaged before the obtaining in stage 100 of the plastic substrate for printing in stage 200 or directly between stages 100 and 200. The stage of plasma pre-treatment, e.g. stage 50 can be selected from low-pressure oxygen plasma and atmospheric plasma pre-treatment.

In forms of embodiment of the invention the conductive ink is applied in stage 200 with an aerosol jet printing process or an inkjet printing process.

It can be envisaged that, for example, in stage 350 it is checked whether the desired application thickness has been achieved. This can be done either by measuring the produced ink application or by repeating stages 200 and 300 a predetermined number of times, e.g. 5-10 times, in particular 6 times.

In an optional stage 400 the dried(-on) ink application is sintered. Such a sintering process may be necessary in the case of certain inks in order to set a desired conductivity. In particular, the stage of sintering 400 can be selected from thermal sintering and/or photonic sintering, laser sintering, chemical sintering. Preferably thermal sintering at temperatures below 130° C., e.g. 120° C. is carried out, wherein an upper limit can often be predetermined by the properties of the plastic substrate L1. Laser sintering processes allow location-selective sintering, i.e. the sintering and the degree of sintering can be specifically set depending on the location so that the properties of electrical elements E1, E2 can be specifically influenced. Chemical sintering can be achieved, for example, through subsequent treatment in a bath. For example, the dried(-on) ink application can remain in an aqueous sodium chloride solution (0.9%) for a certain period, e.g. 4 hours.

It can be envisaged that, for example, in a stage 450 it is checked whether a desired sintering has been achieved. This can be done either through measuring the produced ink application or by repeating stage 400 a predetermined number of times, e.g. 5-10 times, in particular 6 times.

It should be noted that several sintering stages of a different nature can be carried out parallel in time, overlapping in time or not overlapping in time. For example it would be possible to initially envisage a thermal sintering stage and thereafter to carry out a chemical sintering stage.

In one form of embodiment of the invention, on application to the plastic substrate L1 the conductive ink comprises at least 10 percent by weight metallic parts and at least one solvent. In particular, the conductive ink 105 comprises gold or 30%, . . . 40%, . . . 50% silver. In forms of embodiment of the invention the ink comprises a solvent, in particular an alcohol, more particularly ethylene glycol, i.e. in forms of embodiment the ink can be a nanoparticle metal ink.

In a particularly advantageous form of embodiment of the process according to the invention, a nanoparticle silver ink with 30% by weight silver and ethylene glycol as the solvent is applied by means of an aerosol jet printing process onto a substrate of polycarbonate or COC which has been previously been plasma pre-treated and then photonically sintered. In addition, in this particularly advantageous form of embodiment chemical sintering takes place after the photonic sintering in that the printed electronic component is brought into contact with a sodium chloride solution, for example. An advantage of this form of embodiment is that particularly high conductance values of the printed electronic component can be achieved.

In a further particularly advantageous form of embodiment of the process according to the invention a silver ink with a 40% portion by weight is applied by means of an aerosol jet process onto a substrate of polycarbonate or COC which has previously been plasma pre-treated. In this particularly advantageous form of embodiment three layers of ink are applied and then photonically sintered. An advantage of this form of embodiment is that particularly high conductance values of the printed electronic component can be achieved.

In forms of embodiment of the invention the printable electrical component is produced with an ink containing gold and, for example, is used in the interior of a fluid line.

The invention claimed is:

1. A medical device comprising a printable electrical component, the printable electrical component comprising a plastic substrate that is flexible and has a thickness of 2 mm or less, wherein at least one electrical component is applied to the plastic substrate, wherein the electrical component comprises a dried conductive ink, wherein the plastic substrate is at least one of polycarbonate, cycloolefin copolymers, polymethyl-methacrylate, and polypropylene and wherein the dried, conductive ink comprises silver and/or gold, wherein the electrical component comprises at least one conductor section or at least two electrodes, and the medical device further comprises a fluid line having a fluid line wall, wherein the printable electrical component is located on an outside of the fluid line wall such that the printable electrical component measures properties of a fluid through the fluid line wall and the electrical component is part of an expansion sensor and/or a temperature sensor and/or a conductivity sensor and/or a pressure sensor and/or a thermal flow sensor.

2. The medical device according to claim 1, wherein the electrical component is a resistor.

3. The medical device according to claim 1, wherein the printable electrical component is biocompatible.

4. The medical device according to claim 1, wherein the printable electrical component is not biodegradable.

5. The medical device according to claim 1, wherein the dried conductive ink is covered with a protective layer.

6. The medical device according to claim 5, wherein the protective layer has an insulating effect, wherein on the protective layer a further electrical component is applied, wherein the further electrical component comprises a dried conductive ink.

7. The medical device according to claim 1, wherein the medical device is an element of a dialysis device.

8. The medical device according to claim 1, wherein the medical device is a disposable consumable element of a dialysis device.

9. A wearable for wearing on a body comprising the medical device according to claim 1.

10. The wearable according to claim 9 wherein the printable electrical component is arranged on an elastic strap so that the elastic strap can be slung around the body or a part of the body of a mammal and contacting it.

11. A method comprising: performing dialysis on a patient using a dialysis system comprising the medical device according to claim 1.

* * * * *